(12) United States Patent
Higuchi

(10) Patent No.: US 11,028,434 B2
(45) Date of Patent: *Jun. 8, 2021

(54) EXPONENTIAL BASE-GREATER-THAN-2 NUCLEIC ACID AMPLIFICATION

(71) Applicant: Cepheid, Sunnyvale, CA (US)

(72) Inventor: Russell Higuchi, Alameda, CA (US)

(73) Assignee: CEPHEID, Sunnyvale, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/359,947

(22) Filed: Mar. 20, 2019

(65) Prior Publication Data

US 2019/0203266 A1  Jul. 4, 2019

Related U.S. Application Data

(63) Continuation of application No. 15/535,009, filed as application No. PCT/US2015/065890 on Dec. 15, 2015, now Pat. No. 10,273,534.

(60) Provisional application No. 62/092,102, filed on Dec. 15, 2014.

(51) Int. Cl.
C12Q 1/68 (2018.01)
C12Q 1/686 (2018.01)

(52) U.S. Cl.
CPC ....... *C12Q 1/686* (2013.01); *C12Q 2525/155* (2013.01); *C12Q 2525/161* (2013.01); *C12Q 2525/191* (2013.01); *C12Q 2531/119* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,958,349 A | 9/1999 | Petersen et al. |
| 6,403,037 B1 | 6/2002 | Chang et al. |
| 6,440,725 B1 | 8/2002 | Pourahmadi et al. |
| 6,783,736 B1 | 8/2004 | Taylor et al. |
| 6,818,185 B1 | 11/2004 | Petersen et al. |
| 8,252,558 B2 | 8/2012 | Fu |
| 8,871,469 B1 | 10/2014 | Benner et al. |
| 2012/0122161 A1* | 5/2012 | Musgrave-Brown ........ C12Q 1/6809 435/91.21 |
| 2013/0323738 A1* | 12/2013 | Tanner ................ C12Q 1/6853 435/6.12 |

(Continued)

FOREIGN PATENT DOCUMENTS

| | | |
|---|---|---|
| CN | 1420928 A | 5/2003 |
| JP | 2008-029335 A | 2/2008 |

(Continued)

OTHER PUBLICATIONS

U.S. Office Action (Restriction Requirement) dated Feb. 15, 2018 issued in U.S. Appl. No. 15/535,009.

(Continued)

*Primary Examiner* — Aaron A Priest
(74) *Attorney, Agent, or Firm* — Emily M. Haliday; Weaver Austin Villeneuve & Sampson LLP

(57) ABSTRACT

Described herein are methods and compositions that provide highly efficient nucleic acid amplification. In some embodiments, this allows a greater than 2-fold increase of amplification product for each amplification cycle and therefore increased sensitivity and speed over conventional PCR.

27 Claims, 5 Drawing Sheets

Specification includes a Sequence Listing.

(56) References Cited

U.S. PATENT DOCUMENTS

| | | |
|---|---|---|
| 2014/0255928 A1 | 9/2014 | Belousov et al. |
| 2014/0296090 A1 | 10/2014 | Mir et al. |
| 2018/0066304 A1 | 3/2018 | Higuchi |
| 2020/0239878 A1 | 7/2020 | Higuchi |

FOREIGN PATENT DOCUMENTS

| | | |
|---|---|---|
| JP | 2008-048648 A | 3/2008 |
| KR | 20130107881 A | 10/2013 |
| WO | WO 95/12309 | 5/1995 |
| WO | WO 02/090538 A1 | 11/2002 |
| WO | WO 03/074724 A2 | 9/2003 |
| WO | WO 2004/044240 | 5/2004 |
| WO | WO 2004/068112 A2 | 8/2004 |
| WO | WO 2016/100388 | 6/2016 |
| WO | WO 2019/162529 A1 | 8/2019 |
| WO | WO 2020/092134 A1 | 5/2020 |

OTHER PUBLICATIONS

U.S. Notice of Allowance dated Dec. 14, 2018 issued in U.S. Appl. No. 15/535,009.
PCT International Search Report and Written Opinion dated Apr. 12, 2016 issued in PCT/US2015/065890.
PCT International Preliminary Report on Patentability and Written Opinion dated Jun. 20, 2017 issued in PCT/US2015/065890.
Harris et al. (Feb. 2013) "Polymerase chain displacement reaction" *BioTechniques* 54:93-97.
Jung et al. (Jan. 15, 2011) "Real-time colorimetric detection of target DNA using isothermal target and signaling probe amplification and gold nanoparticle cross-linking assay" *Biosensors* and *Bioelectronics* 26(5): 1953-1958.
Mitani et al. (Mar. 2007) "Rapid SNP diagnostics using asymmetric isothermal amplification and a new mismatch-suppression technology" *Nat Methods*. 4(3): 257-62 (Epub Feb. 18, 2007).
U.S. Appl. No. 10,273,534, Apr. 30, 2019, Higuchi.
PCT International Search Report and Written Opinion dated Jan. 20, 2020 issued in PCT/US2019/057958.
Chinese Office Action with Search Report dated Jun. 23, 2020 issued in CN 201580076131.0.
Japanese Office Action dated Dec. 2, 2019 issued in JP 2017-550468.
Hoshika et al. (Jul. 26, 2010) "Artificial Genetic Systems. Self-Avoiding DNA in PCR and Multiplexed PCR" *Angew Chem Int Ed Engl*. 49(32): 5554-5557 [HHS Public Access—Author manuscript 10 pages], doi:10.1002/anie.201001977.
Lahoud et al. (Apr. 29, 2008) "Enzymatic synthesis of structure-free DNA with pseudo-complementary properties" *Nucleic Acids Research* 36(10): 3409-3419.
Lahoud et al. (Nov. 5, 2008) "Properties of pseudo-complementary DNA substituted with weakly pairing analogs of guanine or cytosine" *Nucleic Acids Research* 36(22): 6999-7008.
Xu et al. (Feb. 3, 2012) "Cross Priming Amplification: Mechanism and Optimization for Isothermal DNA Amplification" *Scientific Reports* 2: 246 (7 pages) DOI: 10.1038/srep00246.
Yang et al. (Jun. 15, 2015) "Helicase Dependent Isothermal Amplification of DNA and RNA using Self-Avoiding Molecular Recognition Systems" *Chembiochem*. 16(9): 1365-1370 [HHS Public Access—Author manuscript 14 pages], doi:10.1002/cbic.201500135.

\* cited by examiner

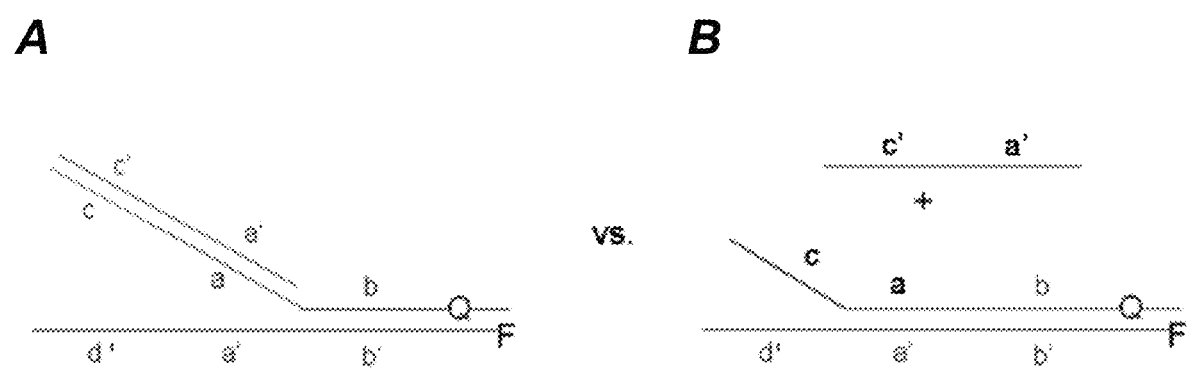
Fig. 6A-B

A
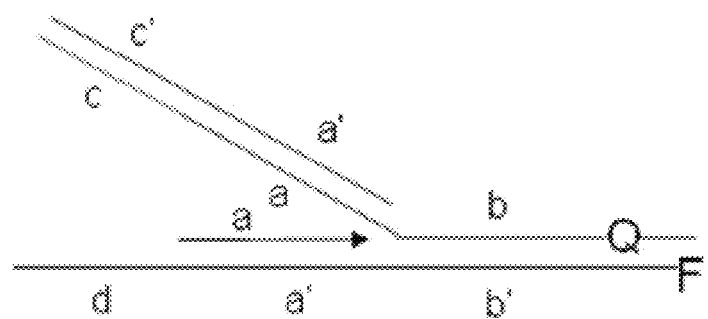
B
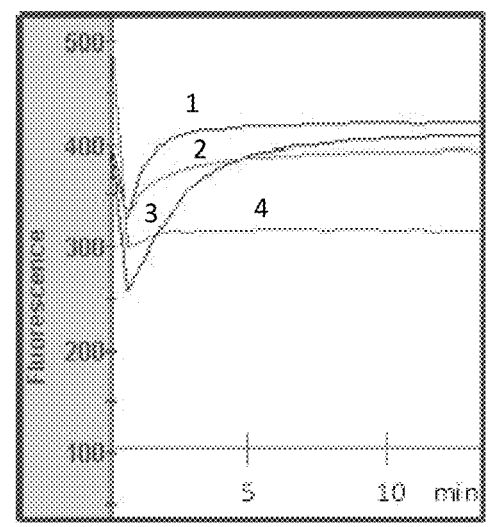
*Fig. 7A-B*

US 11,028,434 B2

EXPONENTIAL BASE-GREATER-THAN-2 NUCLEIC ACID AMPLIFICATION

CROSS-REFERENCE TO RELATED APPLICATIONS

This application is a continuation of U.S. non-provisional application Ser. No. 15/535,009, filed Jun. 9, 2017, which is a U.S. 371 National Phase Application of PCT/US2015/065890, filed Dec. 15, 2015, which claims the benefit of U.S. provisional application No. 62/092,102, filed Dec. 15, 2014, which is hereby incorporated by reference in its entirety.

INCORPORATION BY REFERENCE OF THE SEQUENCE LISTING

This application includes a sequence listing which has been submitted electronically in ASCII format and is hereby incorporated by reference in its entirety. This ASCII copy, created on Mar. 20, 2019, is named 2019-03-20_CPHDP007C1US_SeqList_ST25.txt and is 2,358 bytes in size.

STATEMENT AS TO RIGHTS TO INVENTIONS MADE UNDER FEDERALLY SPONSORED RESEARCH AND DEVELOPMENT

Not applicable.

FIELD

The methods and compositions described herein relate generally to the area of nucleic acid amplification. In particular, described herein are methods and compositions for increasing amplification efficiency.

BACKGROUND

A wide variety of nucleic acid amplification methods are available, and many have been employed in the implementation of sensitive diagnostic assays based on nucleic acid detection. Polymerase chain reaction (PCR) remains the most widely used DNA amplification and quantitation method. Nested PCR, a two-stage PCR, is used to increase the specificity and sensitivity of the PCR (U.S. Pat. No. 4,683,195). Nested primers for use in the PCR amplification are oligonucleotides having sequence complementary to a region on a target sequence between reverse and forward primer targeting sites. However, PCR in general has several limitations. PCR amplification can only achieve less than two fold increase of the amount of target sequence at each cycle. It is still relatively slow. In addition, the sensitivity of this method is typically limited, making it difficult to detect target that may be present at only a few molecules in a single reaction.

SUMMARY

Described herein are methods and compositions based on the use of novel primers (e.g., novel inner primers) designed to so that the outer primer binding site is maintained in the amplicons produced upon amplification.

Provided herein are the following embodiments: Embodiment 1: A nucleic acid primer set for amplifying a target nucleic acid in a sample, wherein the target nucleic acid includes a first template strand and, optionally, a second template strand, wherein the second template strand is complementary to the first template strand, the primer set including oligonucleotides in the form of, or capable of forming, at least two first primers capable of hybridizing to the first template strand, wherein the at least two first primers include a first outer primer and a first inner primer, the first outer primer including a primer sequence a that specifically hybridizes to first template strand sequence a'; and the first inner primer including a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence including:

a primer sequence a adjacent to, and 5' of, single-stranded primer sequence b; and a clamp sequence c adjacent to, and 5' of, primer sequence a, wherein clamp sequence c is not complementary to a first strand template sequence d', which is adjacent to, and 3' of, first strand template sequence a'.

Embodiment 2

The primer set of embodiment 1, wherein the primer set additionally includes at least one second primer capable of specifically hybridizing to the second template strand.

Embodiment 3

A method for amplifying a target nucleic acid in a sample, wherein the target nucleic acid includes a first template strand and, optionally, a second template strand, wherein the second template strand is complementary to the first template strand, the method including:

(a) contacting the sample with:

(i) at least two first primers capable of hybridizing to the first template strand, wherein the at least two first primers comprise a first outer primer and a first inner primer, the first outer primer including a primer sequence a that specifically hybridizes to first template strand sequence a'; and the first inner primer including a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence including:

a primer sequence a adjacent to, and 5' of, single-stranded primer sequence b; and a clamp sequence c adjacent to, and 5' of, primer sequence a, wherein clamp sequence c is not complementary to a first strand template sequence d', which is adjacent to, and 3' of, first strand template sequence a'; and (ii) at least one second primer capable of specifically hybridizing to the second template strand, wherein the contacting is carried out under conditions wherein the primers anneal to their template strands, if present; and (b) amplifying the target nucleic acid, if present, using a DNA polymerase lacking 5'-3' exonuclease activity, under conditions where strand displacement occurs, to produce amplicons that comprise sequence extending from template sequence a' to the binding site for the second primer.

Embodiment 4

The primer set or method of any preceding embodiment, wherein the DNA polymerase includes strand displacement activity.

Embodiment 5

The primer set or method of any preceding embodiment, wherein the $T_m$ of combined sequence c-a, in double-stranded form, is greater than that of combined sequence a-b, in double stranded form.

Embodiment 6

The primer set or method of any preceding embodiment, wherein combined sequence c-a is more GC-rich than combined sequence a-b, and/or contains more stabilizing bases.

Embodiment 7

The method of embodiments 3-6, wherein said amplifying amplifies the target nucleic acid at the rate of up to $3^{number\ of\ cycles}$ during the exponential phase of PCR.

Embodiment 8

The method of embodiments 3-7, wherein said amplifying permits detection of a single copy nucleic acid in a biological sample within about 12%-42% fewer amplification cycles than would be required for said detection using only a single forward and a single reverse primer.

Embodiment 9

The primer set of embodiments 1, 2, 5, or 6 or the method of embodiments 3-8, wherein the second primer includes oligonucleotides in the form of, or capable of forming, at least two second primers capable of hybridizing to the second template strand, wherein the at least two second primers comprise a second outer primer and a second inner primer, the second outer primer including a primer sequence e that specifically hybridizes to second template strand sequence e';

and the second inner primer including a single-stranded primer sequence f that specifically hybridizes to second template strand sequence f, wherein f' is adjacent to, and 5' of, e', and wherein single-stranded primer sequence f is linked at its 5' end to a first strand of a double-stranded primer sequence including:

a primer sequence e adjacent to, and 5' of, single-stranded primer sequence f; and
  a clamp sequence g adjacent to, and 5- of, primer sequence e, wherein clamp sequence g is not complementary to second strand template sequence h', which is adjacent to, and 3', of second strand template sequence e'.

Embodiment 10

The primer set or method of embodiment 9, wherein the $T_m$ of combined sequence g-e, in double-stranded form is greater than that of combined sequence e-f, in double-stranded form.

Embodiment 11

The primer set or method of embodiments 9 or 10, wherein combined sequence g-e is more GC-rich than combined sequence e-f, and/or contains more stabilizing bases.

Embodiment 12

The primer set or method of embodiments 9-11, wherein said amplifying amplifies the target nucleic acid at the rate of up to $6^{number\ of\ cycles}$ during the exponential phase of PCR.

Embodiment 13

The primer set or method of embodiments 9-12, wherein said amplifying permits detection of a single copy nucleic acid in a biological sample within about 36%-66% fewer amplification cycles than would be required for said detection using only a single forward and a single reverse primer.

Embodiment 14

The primer set or method of any preceding embodiment, wherein clamp sequence(s) c and g, if present, is/are not capable of being copied during amplification.

Embodiment 15

The primer set or method of embodiment 14, wherein clamp sequence(s) c and/or g, if present, comprise(s) 2'-O-methyl RNA.

Embodiment 16

The primer set or method of any preceding embodiment, wherein the double-stranded primer sequence of the first inner primer and/or the second inner primer, if present, does not include a hairpin sequence.

Embodiment 17

The primer set or method of embodiments 3-15, wherein the double-stranded primer sequence of the first inner primer includes a hairpin sequence in which clamp sequence c is linked to complementary sequence c' and/or the double-stranded primer sequence of the second inner primer, if present, includes a hairpin sequence in which clamp sequence g is linked to complementary sequence g'.

Embodiment 18

A nucleic acid primer set for amplifying a target nucleic acid in a sample, wherein the target nucleic acid includes a first template strand and, optionally, a second template strand, wherein the second template strand is complementary to the first template strand, the primer set including oligonucleotides in the form of, or capable of forming, at least three first primers capable of hybridizing to the first template strand, wherein the at least three first primers comprise a first outer primer, a first intermediate primer, and a first inner primer, the first outer primer including a primer sequence d that specifically hybridizes to first template strand sequence d';

the first intermediate primer including a primer sequence a that specifically hybridizes to first template strand sequence a', wherein a' is adjacent to, and 5' of, d', and wherein single-stranded primer sequence a is linked at its 5' end to a first strand of a double-stranded primer sequence including:
- a primer sequence d adjacent to, and 5' of, single-stranded primer sequence a; and
- a clamp sequence c1 adjacent to, and 5- of, primer sequence d, wherein clamp sequence c1 is not complementary to a first strand template sequence i', which is adjacent to, and 3' of, first strand template sequence d'; and the first inner primer including a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence including:
- a primer sequence a adjacent to, and 5' of, single-stranded primer sequence b;
- a primer sequence d adjacent to, and 5' of, primer sequence a; and
- a clamp sequence c2 adjacent to, and 5' of, primer sequence d, wherein clamp sequence c2 is not complementary to first strand template sequence i'.

Embodiment 19

The primer set of embodiment 18, wherein the primer set additionally includes at least one second primer capable of specifically hybridizing to the second template strand.

Embodiment 20

A method for amplifying a target nucleic acid in a sample, wherein the target nucleic acid includes a first template strand and, optionally, a second template strand, wherein the second template strand is complementary to the first template strand, the method including:
(a) contacting the sample with:
(i) at least three first primers capable of hybridizing to the first template strand, wherein the at least three first primers comprise a first outer primer, a first intermediate primer, and a first inner primer,
  the first outer primer including a primer sequence d that specifically hybridizes to first template strand sequence d';
  the first intermediate primer including a primer sequence a that specifically hybridizes to first template strand sequence a', wherein a' is adjacent to, and 5' of, d', and wherein single-stranded primer sequence a is linked at its 5' end to a first strand of a double-stranded primer sequence including:
  - a primer sequence d adjacent to, and 5' of, single-stranded primer sequence a; and
  - a clamp sequence c1 adjacent to, and 5- of, primer sequence d, wherein clamp sequence c1 is not complementary to a first strand template sequence i', which is adjacent to, and 3' of, first strand template sequence d'; and
  the first inner primer including a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence including:
  - a primer sequence a adjacent to, and 5' of, single-stranded primer sequence b;
  - a primer sequence d adjacent to, and 5' of, primer sequence a; and
  - a clamp sequence c2 adjacent to, and 5' of, primer sequence d, wherein clamp sequence c2 is not complementary to first strand template sequence i'; and
(ii) at least one second primer capable of specifically hybridizing to the second template strand, wherein the contacting is carried out under conditions wherein the primers anneal to their template strands, if present; and
(b) amplifying the target nucleic acid, if present, using a DNA polymerase lacking 5'-3' exonuclease activity, under conditions where strand displacement occurs, to produce amplicons that comprise sequence extending from template sequence a' to the binding site for the second primer.

Embodiment 21

The primer set or method of embodiments 18-20, wherein the DNA polymerase includes strand displacement activity.

Embodiment 22

The primer set or method of embodiments 18-21, wherein g1 has a different sequence than g2.

Embodiment 23

The primer set or method of embodiments 18-22, wherein the $T_m$ of combined sequence c1-$d$, in double-stranded form, is greater than that of combined sequence d-a, in double-stranded form, and the $T_m$ of combined sequence c2-$d$-$a$, in double-stranded form, is greater than that of combined sequence d-a-b, in double-stranded form.

Embodiment 24

The primer set or method of embodiments 18-23, wherein combined sequence c1-$d$ is more GC-rich than combined sequence d-a, and/or contains more stabilizing bases, and combined sequence c2-$d$-$a$ is more GC-rich than combined sequence d-a-b, and/or contains more stabilizing bases than combined sequence d-a-b.

Embodiment 25

The method of embodiments 20-24, wherein said amplifying amplifies the target nucleic acid at the rate of up to $4^{number\ of\ cycles}$ during the exponential phase of PCR.

Embodiment 26

The method of embodiments 20-25, wherein said amplifying permits detection of a single copy nucleic acid in a biological sample within about 25%-55% fewer amplification cycles than would be required for said detection using only a single forward and a single reverse primer.

Embodiment 27

The primer set or method of embodiments 18-26, wherein the second primer includes oligonucleotides in the form of, or capable of forming, at least three second primers capable of hybridizing to the second template strand, wherein the at least three second primers comprise a second outer primer, a second intermediate primer, and a second inner primer, the second outer primer including a primer sequence h that specifically hybridizes to second template strand sequence h';

the second intermediate primer including a single-stranded primer sequence e that specifically hybridizes to second template strand sequence e', wherein e' is adjacent to, and 5' of, h', and wherein single-stranded primer sequence e is linked at its 5' end to a first strand of a double-stranded primer sequence including:
- a primer sequence h adjacent to, and 5' of, single-stranded primer sequence e; and
- a clamp sequence g1 adjacent to, and 5' of, primer sequence h, wherein clamp sequence g1 is not complementary to a second strand template sequence j', which is adjacent to, and 3', of second strand template sequence h'; and the second inner primer including a single-stranded primer sequence f that specifically hybridizes to first template strand sequence f', wherein f' is adjacent to, and 5' of, e', and wherein single-stranded primer sequence f is linked at its 5' end to a first strand of a double-stranded primer sequence including:
- a primer sequence e adjacent to, and 5' of, single-stranded primer sequence f;
- a primer sequence h adjacent to, and 5' of, primer sequence e; and
- a clamp sequence g2 adjacent to, and 5' of, primer sequence h, wherein clamp sequence c2 is not complementary to first strand template sequence j'.

Embodiment 28

The primer set or method of embodiment 27, wherein the $T_m$ of combined sequence g1-h, in double-stranded form, is greater than that of combined sequence h-e, in double-stranded form, and the $T_m$ of combined sequence g2-h-e, in double-stranded form, is greater than that of combined sequence h-e-f, in double-stranded form.

Embodiment 29

The primer set or method of embodiments 27 or 28, wherein combined sequence g1-h is more GC-rich than combined sequence h-e, and/or contains more stabilizing bases, and combined sequence g2-h-e is more GC-rich than combined sequence h-e-f, and/or contains more stabilizing bases than combined sequence h-e-f.

Embodiment 30

The method of embodiments 27-29, wherein said amplifying amplifies the target nucleic acid at the rate of up to $8^{number\ of\ cycles}$ during the exponential phase of PCR.

Embodiment 31

The method of embodiments 27-30, wherein said amplifying permits detection of a single copy nucleic acid in a biological sample within about 42%-72% fewer amplification cycles than would be required for said detection using only a single forward and a single reverse primer.

Embodiment 32

The primer set or method of embodiments 18-31, wherein clamp sequences c1 and c2, and g1 and g2, if present, are not capable of being copied during amplification.

Embodiment 33

The primer set or method of embodiment 32, wherein clamp sequences c1 and c2, and g1 and g2, if present, include 2'-O-methyl RNA.

Embodiment 34

The primer set or method of embodiments 20-33, wherein: the double-stranded primer sequence of the first inner primer and the first intermediate primer; and/or the second inner primer and the second intermediate primer, if present, does/do not comprise a hairpin sequence.

Embodiment 35

The primer set or method of embodiments 20-33, wherein: the double-stranded primer sequence of the first inner primer includes a hairpin sequence in which clamp sequence c2 is linked to complementary sequence c2'; and/or the double-stranded primer sequence of the first intermediate primer includes a hairpin sequence in which clamp sequence c1 is linked to complementary sequence c1'; and/or the double-stranded primer sequence of the second inner primer, if present, includes a hairpin sequence in which clamp sequence g2 is linked to complementary sequence g2'; and/or the double-stranded primer sequence of the second intermediate primer, if present, includes a hairpin sequence in which clamp sequence g1 is linked to complementary sequence g1'.

Embodiment 36

The method of embodiments 3-17 or 20-35, wherein the amplification includes PCR.

Embodiment 37

The method of embodiments 3-17 or 20-36, wherein the DNA polymerase includes strand displacement activity and is thermostable.

Embodiment 38

The method of embodiments 3-17 or 20-37, wherein the method includes detecting, and optionally quantifying, the target nucleic acid.

Embodiment 39

The method of embodiments 3-17 or 20-38, wherein the sample consists of nucleic acids from a single cell.

Embodiment 40

The primer set or method of any of embodiments 1-6, wherein combined sequence a-b contains more destabilizing bases than combined sequence c-a.

Embodiment 41

The primer set or method of embodiments 9-11, wherein combined sequence e-f contains more destabilizing bases than combined sequence g-e.

Embodiment 42

The primer set or method of embodiments 18-24, wherein combined sequence d-a contains more destabilizing bases than combined sequence c1-d, and/or combined sequence d-a-b contains more destabilizing bases than combined sequence c2-d-a.

Embodiment 43

The primer set or method of embodiments 27-29, wherein combined sequence h-e contains more destabilizing bases than combined sequence g1-h, and/or combined sequence h-e-f contains more destabilizing bases than combined sequence g2-h-e.

BRIEF DESCRIPTION OF THE DRAWINGS

FIG. 6A-B: A schematic drawing showing two alternative structures for the illustrated primer having a clamp sequence when the primer is allowed to hybridize with template. A fluorescent quencher (Q) is present in the primer in a position where it quenches a corresponding fluorescent label (F) in the template strand. In Example 1, an experiment was performed in which the Tm was measured of the primer and a complimentary target sequence with and without the clamp present. (A) The structure formed if the $T_m$ of combined sequence c-a, in double-stranded form, is greater than that of combined sequence a-b, in double stranded form. (B) The structure formed if the $T_m$ of combined sequence c-a, in double-stranded form, is less than that of combined sequence a-b, in double stranded form.

FIG. 7A-B: (A) A schematic showing an illustrative two-primer set in which a fluorescent quencher (Q) is present in the inner primer in a position where it quenches a corresponding fluorescent label (F) in the template strand. (B) Fluorescence intensity as a function of time from the primer extension reaction of Example 2. The three rising traces are separate reactions with slightly different clamps; the flat trace is without the outer (flanking), displacing primer present.

DETAILED DESCRIPTION

Definitions

Figure 1:
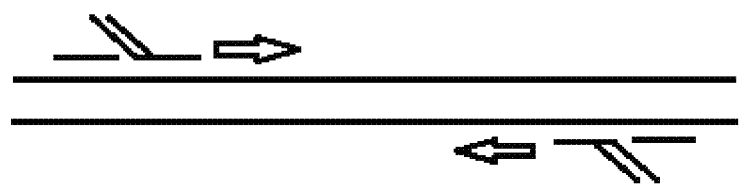
FIG. 1: A schematic showing fully nested PCR being carried out on a double-stranded DNA template. The flanking primers are as described for FIG. 2 and FIG. 3.

Terms used in the claims and specification are defined as set forth below unless otherwise specified.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; mRNA; and non-coding RNA.

The term nucleic acid encompasses double- or triple-stranded nucleic acid complexes, as well as single-stranded molecules. In double- or triple-stranded nucleic acid complexes, the nucleic acid strands need not be coextensive (i.e, a double-stranded nucleic acid need not be double-stranded along the entire length of both strands).

The term nucleic acid also encompasses any chemical modifications thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, sugar-phosphate backbone modifications, unusual base pairing combinations such as the isobases isocytidine and isoguanidine, and the like.

More particularly, in some embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino polymers (commercially available from the Anti-Virals, Inc., Corvallis, Oreg., as Neugene), and other synthetic sequence-specific nucleic acid polymers providing that the polymers contain nucleobases in a configuration which allows for base pairing and base stacking, such as is found in DNA and RNA. The term nucleic acid also encompasses locked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

As used herein, the term "complementary" refers to the capacity for precise pairing between two nucleotides; i.e., if a nucleotide at a given position of a nucleic acid is capable of hydrogen bonding with a nucleotide of another nucleic acid to form a canonical base pair, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In some embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference for their descriptions of stringent hybridization conditions). As indicated by standard references, a simple estimate of the $T_m$ value may be calculated by the equation: $T_m=81.5+0.41(\% \text{ G+C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7. Tm calculation for oligonuclotide sequences based on nearest-neighbors thermodynamics can carried out as described in "A unified view of polymer, dumbbell, and oligonucleotide DNA nearest-neighbor thermodynamics" John SantaLucia, Jr., PNAS Feb. 17, 1998 vol. 95 no. 4 1460-1465 (which is incorporated by reference herein for this description).

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, in some embodiments, range from 10 to 30 nucleotides, or, in some embodiments, from 10 to 60 nucleotides, in length. In some embodiments, primers can be, e.g., 15 to 50 nucleotides long. Short primer molecules generally require cooler temperatures to form sufficiently stable hybrid complexes with the template. A primer need not reflect the exact sequence of the template but must be sufficiently complementary to hybridize with a template.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in some embodiments, amplification primers used herein are said to "anneal to" or be "specific for" a nucleotide sequence." This description encompasses primers that anneal wholly to the nucleotide sequence, as well as primers that anneal partially to the nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientations in some embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

The primer or probe can be perfectly complementary to the target nucleotide sequence or can be less than perfectly complementary. In some embodiments, the primer has at least 65% identity to the complement of the target nucleotide sequence over a sequence of at least 7 nucleotides, more typically over a sequence in the range of 10-30 nucleotides, and, in some embodiments, over a sequence of at least 14-25 nucleotides, and, in some embodiments, has at least 75% identity, at least 85% identity, at least 90% identity, or at least 95%, 96%, 97%, 98%, or 99% identity. It will be understood that certain bases (e.g., the 3' base of a primer) are generally desirably perfectly complementary to corresponding bases of the target nucleotide sequence. Primer and probes typically anneal to the target sequence under stringent hybridization conditions.

As used herein with reference to a portion of a primer or a nucleotide sequence within the primer, the term "specific for" a nucleic acid, refers to a primer or nucleotide sequence that can specifically anneal to the target nucleic acid under suitable annealing conditions.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include PCR, nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), helicase-dependent amplification (HDA), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

"Nested amplification" refers the use of more than two primers to amplify a target nucleic acid.

"Hemi-nested amplification" refers to the use of more than one primer (e.g., two or three) that anneal at one end of a target nucleotide sequence.

"Fully nested amplification" refers to the use of more than one primer that anneal at each end of a target nucleotide sequence.

With reference to nested amplification, the multiple primers that anneal at one end of an amplicon are differentiated by using the terms "inner," "outer," and "intermediate."

An "outer primer" refers to a primer that that anneals to a sequence closer to the end of the target nucleotide sequence than another primer that anneals at that same end of the target nucleotide sequence. In some embodiments, the outer primer sequence defines the end of the amplicon produced from the target nucleic acid. The "outer primer" is also referred to herein as a "flanking primer."

An "inner primer" refers to a primer that that anneals to a sequence closer to the middle of the target nucleotide sequence than another primer that anneals at that same end of the target nucleotide sequence.

The term "intermediate primer" is used herein with reference to nest amplification in which at least three primers that anneal at one end of a target nucleotide sequence are used. An intermediate primer is one that anneals to a sequence in between an inner primer and an outer primer.

As used herein, the term "adjacent to" is used to refer to sequences that are in sufficiently close proximity for the methods to work. In some embodiments, sequences that are adjacent to one another are immediately adjacent, with no intervening nucleotides.

A "multiplex amplification reaction" is one in which two or more nucleic acids distinguishable by sequence are amplified simultaneously.

The term "qPCR" is used herein to refer to quantitative real-time polymerase chain reaction (PCR), which is also known as "real-time PCR" or "kinetic polymerase chain reaction;" all terms refer to PCR with real-time signal detection.

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, dNTPs, and the like. Reagents for enzyme reactions include, for example, substrates, cofactors, buffer, metal ions, inhibitors, and activators.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser or another fluorescent dye.

General Approach for Increasing Amplification Efficiency

U.S. Pat. No. 8,252,558 and Harris et al., BioTechniques 54:93-97 (February 2013) teach a form of nested PCR, termed "Polymerase Chain Displacement Reaction" (PCDR) (both documents are incorporated by reference herein for this description). In PCDR, when extension occurs from an outer primer, it displaces the extension strand produced from an inner primer because the reaction employs a polymerase that has strand displacement activity. In theory, this allows a greater than 2-fold increase of amplification product for each amplification cycle and therefore increased sensitivity and speed over conventional PCR. In practice, every amplicon created from a nested primer no longer contains a primer annealing site for the outer primer. Accordingly, PCDR cannot sustain a greater than 2-fold increase of amplification product for each amplification cycle for very many cycles. For this reason, PCDR offers only modest reduction in the number of amplification cycles (e.g., from about 23 to about 20) needed to detect a target nucleic acid. By contrast, Table 1 below shows that a sustained quadrupling per cycle ($4^{number\ of\ cycles}$) should halve the number of cycles needed to have the same amplification as a doubling per cycle. A sustained 6-fold replication per cycle should achieve in 15 cycles what would take 40 normal PCR cycles.

TABLE 1

Degree of Amplification With Different "Bases"

| | bases | | | | |
|---|---|---|---|---|---|
| cycles | 2 | 3 | 4 | 5 | 6 |
| 0 | 1 | 1 | 1 | 1 | 1 |
| 1 | 2 | 3 | 4 | 5 | 6 |
| 2 | 4 | 9 | 16 | 25 | 36 |
| 3 | 8 | 27 | 64 | 125 | 216 |
| 4 | 16 | 81 | 256 | 625 | 1296 |
| 5 | 32 | 243 | 1024 | 3125 | 7776 |
| 6 | 64 | 729 | 4096 | 15625 | 46656 |
| 7 | 128 | 2187 | 16384 | 78125 | 279936 |
| 8 | 256 | 6561 | 65536 | 390625 | 1679616 |
| 9 | 512 | 19683 | 262144 | 1953125 | 10077696 |
| 10 | 1024 | 59049 | 1048576 | 9765625 | 60466176 |
| 11 | 2048 | 177147 | 4194304 | 48828125 | 3.63E+09 |
| 12 | 4096 | 531441 | 16777216 | 2.44E+09 | 2.16E+09 |
| 13 | 8192 | 1594323 | 67108864 | 1.22E+09 | 1.31E+10 |
| 14 | 16384 | 4782969 | 2.86E+08 | 6.1E+09 | 7.64E+10 |
| 15 | 32768 | 14348907 | 1.07E+08 | 3.06E+10 | 4.7E+11 |
| 16 | 65536 | 43046721 | 4.28E+08 | 1.63E+11 | 2.62E+12 |
| 17 | 131072 | 1.28E+08 | 1.72E+10 | 7.63E+11 | 1.53E+13 |
| 18 | 262144 | 3.67E+08 | 6.67E+10 | 3.61E+12 | 1.02E+14 |
| 19 | 524288 | 1.16E+08 | 2.75E+11 | 1.91E+12 | 6.09E+15 |
| 20 | 1048576 | 3.43E+09 | 1.1E+12 | 3.54E+13 | 3.66E+15 |
| 21 | 2097152 | 1.06E+10 | 4.4E+12 | 4.77E+14 | 2.19E+16 |
| 22 | 4194304 | 3.14E+10 | 1.75E+13 | 2.36E+15 | 1.32E+17 |

TABLE 1-continued

Degree of Amplification With Different "Bases"

| | bases | | | | |
|---|---|---|---|---|---|
| cycles | 2 | 3 | 4 | 5 | 6 |
| 23 | 8388608 | 8.41E+10 | 7.04E+13 | 1.18E+16 | 7.8E+17 |
| 24 | 16777216 | 2.62E+11 | 2.61E+14 | 5.86E+16 | 4.74E+18 |
| 25 | 33554432 | 8.47E+11 | 1.13E+15 | 2.86E+17 | 2.64E+19 |
| 26 | 67108864 | 2.54E+12 | 4.6E+16 | 1.49E+18 | 1.71E+20 |
| 27 | 1.34E+06 | 7.63E+12 | 1.6E+16 | 7.46E+18 | 1.02E+21 |
| 28 | 2.56E+06 | 2.28E+12 | 7.21E+16 | 3.73E+19 | 6.14E+21 |
| 29 | 6.37E+06 | 6.66E+13 | 2.66E+17 | 1.60E+20 | 3.66E+22 |
| 30 | 1.07E+06 | 2.06E+14 | 1.16E+18 | 9.31E+20 | 2.21E+23 |
| 31 | 2.16E+08 | 6.16E+14 | 4.61E+18 | 4.66E+21 | 1.33E+24 |
| 32 | 4.28E+08 | 1.66E+14 | 1.64E+19 | 2.33E+22 | 7.95E+25 |
| 33 | 6.89E+08 | 6.66E+15 | 7.36E+19 | 1.15E+23 | 4.76E+26 |
| 34 | 1.72E+09 | 1.67E+16 | 2.85E+20 | 5.62E+23 | 2.67E+26 |
| 35 | 3.44E+10 | 6E+18 | 1.18E+21 | 2.91E+24 | 1.72E+27 |
| 36 | 6.67E+10 | 1.6E+17 | 4.72E+21 | 1.45E+25 | 1.03E+28 |
| 37 | 1.37E+11 | 4.6E+17 | 1.68E+22 | 7.26E+25 | 6.16E+28 |
| 38 | 2.75E+11 | 1.36E+18 | 7.55E+22 | 3.64E+25 | 3.71E+29 |
| 39 | 6.6E+11 | 4.06E+18 | 3.02E+23 | 1.62E+27 | 2.23E+30 |
| 40 | 1.1E+12 | 1.22E+18 | 1.21E+24 | 9.08E+27 | 1.34E+31 |

Figure 2:
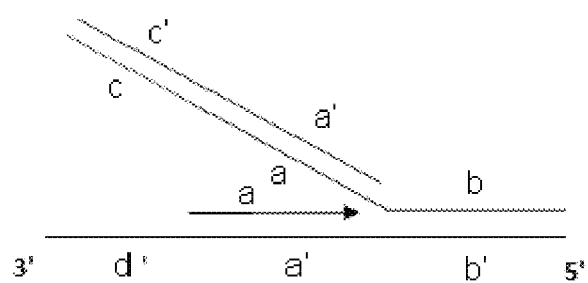
FIG. 2: A schematic showing an illustrative two-primer set hybridized to one end of a target nucleotide sequence. This set can be, e.g., a forward primer set. Different segments of primer sequence are shown (a, b, c); complementary sequences are indicated as (a', b', c'). Template sequences are indicated 3'-5' as d', a', and b'. The outer primer (a) is single-stranded. The inner primer has a single stranded portion (b) and a double-stranded portion (a-c).

A key to sustaining a greater than 2-fold increase of amplification product for each amplification cycle is to design the inner (nested) primer so that the extension product of the inner (nested) primer contains the outer (flanking) primer sequence. FIG. 1 shows a scheme in which fully nested PCR is carried out using a forward inner and outer primer and a reverse inner and outer primer. The "flap" formed when inner primer anneals to template contains the outer primer sequence so that each of the four new strands generated from the two template strands extends from (and includes) either the forward outer primer sequence (or its complement) through (and including) the reverse outer primer sequence. However, more is required than simply appending the outer primer sequence to the 5' end of the inner primer because, when the inner primer anneals, the appended sequence would immediately also anneal and block the outer primer from annealing. A solution to this problem is to use an additional 5' add-on to the inner primer (i.e., a sequence in addition to the outer primer sequence) together with an oligonucleotide complementary to both sequences, which is referred to herein as a "clamp." For ease of discussion, the add-on sequence is termed a "clamp sequence." This configuration is shown in FIG. 2.

The clamp sequence, c, is not homologous to the template (d' region). Here c-a/c'-a' is more stable than a-b/a'-b'. In some embodiments, this can be achieved by employing a sequence c that is long relative to a, GC-rich (i.e., more GC-rich than a), or contains one or more stabilizing bases, when a does not contain such bases, or more stabilizing bases than in a. In some embodiments, this can be achieved by employing a sequence c that is long relative to b, GC-rich (i.e., more GC-rich than b), or contains one or more stabilizing bases, when b does not contain such bases, or more stabilizing bases than in b. In some embodiments, a stabilizing base can be included in the a region of c-a-b, as well as in the a' region of c'-a' to enhance the stability of c-a/c'-a', relative to a-b/a'-b'. Alternatively or in addition, b can contain one or more destabilizing bases, such as inosine. The outer primer remains sequence a. In this case, sequence a' in the template remains available for the outer primer. The c'-a' clamp and the 5' end of the inner primer will rapidly anneal at a higher temperature than any of the other sequences, and therefore it is not necessary that the c'-a' clamp be linked to the inner primer so as to form a hairpin structure. However, in some embodiments, the use of an inner primer having this type of hairpin structure may increase the speed of the reaction.

In some embodiments, the c sequence in the inner primer is preferably not copied during PCR. If it is, then these new templates will have a c'-a' tail that will create with the inner primer a c-a-b/c'-a'-b' duplex that would "win-out" in the strand displacement contest over the other possible structures and, again, prevent the flanking primer, sequence a, from annealing. To prevent this copying, the c sequence can be made from RNA (or 2'-O-methyl RNA, which is relatively easy to make synthetically), which DNA polymerase cannot copy well. This c sequence can be made from any bases capable of base-pairing, but not capable of being copied.

In some embodiments, the clamp oligonucleotide (a'-c') is blocked to extension at the 3' end, e.g., by virtue of lacking a 3' hydroxyl group or using a chemical blocking moiety, which can improve the specificity of the amplification.

Samples

Nucleic acid-containing samples can be obtained from biological sources and prepared using conventional methods known in the art. In particular, nucleic useful in the methods described herein can be obtained from any source, including unicellular organisms and higher organisms such as plants or non-human animals, e.g., canines, felines, equines, primates, and other non-human mammals, as well as humans. In some embodiments, samples may be obtained from an individual suspected of being, or known to be, infected with a pathogen, an individual suspected of having, or known to have, a disease, such as cancer, or a pregnant individual.

Nucleic acids can be obtained from cells, bodily fluids (e.g., blood, a blood fraction, urine, etc.), or tissue samples by any of a variety of standard techniques. In some embodiments, the method employs samples of plasma, serum, spinal fluid, lymph fluid, peritoneal fluid, pleural fluid, oral fluid, and external sections of the skin; samples from the respiratory, intestinal genital, or urinary tracts; samples of tears, saliva, blood cells, stem cells, or tumors. Samples can be obtained from live or dead organisms or from in vitro cultures. Illustrative samples can include single cells, paraffin-embedded tissue samples, and needle biopsies. In some embodiments, the nucleic acids analyzed are obtained from a single cell.

Nucleic acids of interest can be isolated using methods well known in the art. The sample nucleic acids need not be in pure form, but are typically sufficiently pure to allow the steps of the methods described herein to be performed.

Target Nucleic Acids

Any target nucleic acid that can detected by nucleic acid amplification can be detected using the methods described herein. In typical embodiments, at least some nucleotide sequence information will be known for the target nucleic acids. For example, if the amplification reaction employed is PCR, sufficient sequence information is generally available for each end of a given target nucleic acid to permit design of suitable amplification primers.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, and/or mutated) in genetic diseases or other pathologies; sequences that are associated with desirable or undesirable traits; and/or sequences that uniquely identify an individual (e.g., in forensic or paternity determinations).

Primer Design

Primers suitable for nucleic acid amplification are sufficiently long to prime the synthesis of extension products in the presence of a suitable nucleic acid polymerase. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 10 to about 60 nucleotides, although it may contain more or fewer nucleotides. The primers should be sufficiently complementary to selectively anneal to their respective strands and form stable duplexes.

In general, one skilled in the art knows how to design suitable primers capable of amplifying a target nucleic acid of interest. For example, PCR primers can be designed by using any commercially available software or open source software, such as Primer3 (see, e.g., Rozen and Skaletsky (2000) Meth. Mol. Biol., 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; the solid support method of U.S. Pat. No. 4,458,066 and the like, or can be provided from a commercial source. Primers may be purified by using a Sephadex column (Amersham Biosciences, Inc., Piscataway, N.J.) or other methods known to those skilled in the art. Primer purification may improve the sensitivity of the methods described herein.

Outer Primer

Figure 3:
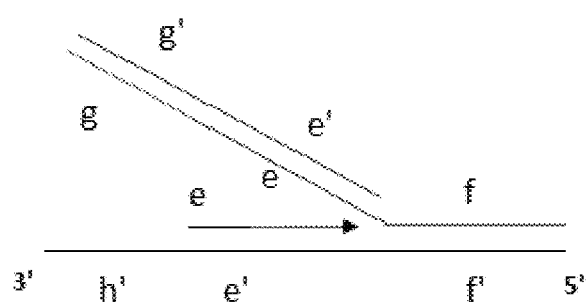
FIG. 3: A schematic showing an illustrative two-primer set hybridized to the opposite end of a target nucleotide sequence from that shown in FIG. 2. This set can be, e.g., a reverse primer set. Different segments of primer sequence are shown (e, f, g); complementary sequences are indicated as (e', f', g'). Template sequences are indicated 3'-5' as h', e', and f'. The outer primer (e) is single-stranded. The inner primer has a single stranded portion (f) and a double-stranded portion (a-g).
Figure 4:
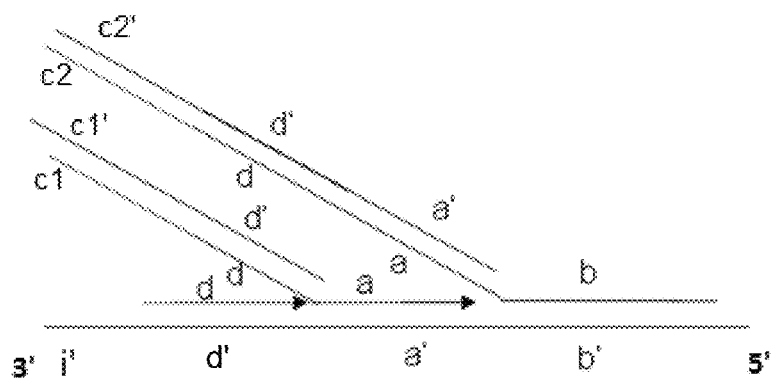
FIG. 4: A schematic showing an illustrative three-primer set hybridized to one end of a target nucleotide sequence. This set can be, e.g., a forward primer set. Different segments of primer sequence are shown (a, b, c1, c2, d); complementary sequences are indicated as (a', b', c1', c2', d'). Template sequences are indicated 3'-5' as i', d', a', and b'. The outer primer (d) is single-stranded. The intermediate primer has a single stranded portion (a) and a double-stranded portion (d-c1). The inner primer has a single stranded portion (b) and a double-stranded portion (a-d-c2).
Figure 5:
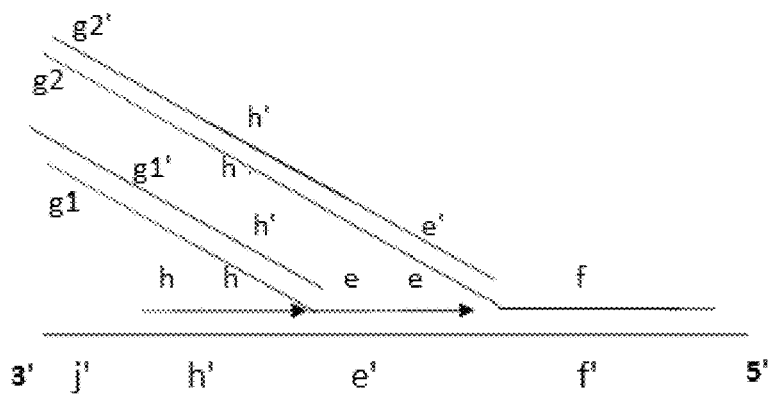
FIG. 5: A schematic showing an illustrative three-primer set hybridized to the opposite end of a target nucleotide sequence from that shown in FIG. 4. This set can be, e.g., a reverse primer set. Different segments of primer sequence are shown (e, f, g1, g2, h); complementary sequences are indicated as (e', f, g1', g2', h'). Template sequences are indicated 3'-5' as j', h', e', and f. The outer primer (d) is single-stranded. The intermediate primer has a single stranded portion (e) and a double-stranded portion (h-g1). The inner primer has a single stranded portion (f) and a double-stranded portion (e-h-g2).

FIG. 2 shows how a two-primer set anneals to a first template strand at one end of a target nucleotide sequence. For ease of discussion, this primer set can be considered to be a "forward" primer set. The outer primer includes a sequence a that specifically hybridizes to first template strand sequence a'. FIG. 3 shows how a two-primer set anneals to a second template strand at the opposite end of the target nucleotide sequence. For ease of discussion, this primer set can be considered to be a "reverse" primer set. Here, the outer primer includes a sequence e that specifically hybridizes to first template strand sequence e'. FIGS. 4 and 5 show illustrative "forward" and "reverse" three-primer sets. In FIG. 4, the forward outer primer includes a sequence d that specifically hybridizes to first template strand sequence d'. In FIG. 5, the forward outer primer includes a sequence d that specifically hybridizes to first template strand sequence d'. In general, the considerations for designing suitable outer primers do not differ from those for designing outer primers for use in conventional nested PCR. Notably, in some embodiments, the $T_m$ of any primer sequence that is "outer" relative to another primer sequence (e.g., an inner or intermediate primer sequence) is preferably lower than the $T_m$ of the inner (or intermediate) primer sequence. Thus, for example, during the down temperature ramp of PCR, the inner primer can anneal and begin extension before the outer primer; otherwise premature extension of the outer primer would block the target site of the inner primer and prevent its annealing. More specifically, in the embodiment shown in FIG. 2, primer sequence a would have a $T_m$ less than that of primer sequence b. Similarly, in the embodiment shown in FIG. 3, primer sequence e would have a lower $T_m$ than primer sequence f. In some embodiments, the $T_m$ differences are at least about 4 degrees, generally in the range of about 4 to about 20 degrees C. In some embodiments, the $T_m$ differences are in the range of about 4 to about 15 degrees C. However, the $T_m$ of the outer primer is generally high enough to maintain efficient PCR, e.g., in some embodiments, the $T_m$ of the outer primer is at least 40 degrees C. $T_m$ can be adjusted by adjusting the length of a sequence, the G-C content, and/or by including stabilizing or destabilizing base(s) in the sequence.

"Stabilizing bases" include, e.g., stretches of peptide nucleic acids (PNAs) that can be incorporated into DNA oligonucleotides to increase duplex stability. Locked nucleic acids (LNAs) and unlocked nucleic acids (UNAs) are analogues of RNA that can be easily incorporated into DNA oligonucleotides during solid-phase oligonucleotide synthesis, and respectively increase and decrease duplex stability. Suitable stabilizing bases also include modified DNA bases that increase the stability of base pairs (and therefore the duplex as a whole). These modified bases can be incorporated into oligonucleotides during solid-phase synthesis and offer a more predictable method of increasing DNA duplex stability. Examples include AP-dC (G-clamp) and 2-aminoadenine, as well as 5-methylcytosine and C(5)-propynylcytosine (replacing cytosine), and C(5)-propynyluracil (replacing thymine).

"Destabilizing bases" are those that destabilize double-stranded DNA by virtue of forming less stable base pairs than the typical A-T and/or G-C base pairs. Inosine (I) is a destabilizing base because it pairs with cytosine (C), but an I-C base pair is less stable than a G-C base pair. This lower stability results from the fact that inosine is a purine that can make only two hydrogen bonds, compared to the three hydrogen bonds of a G-C base pair. Other destabilizing bases are known to, or readily identified by, those of skill in the art.

Inner Primer of a Two-Primer Set

Referring to FIG. 2, the inner primer in a forward two-primer set includes a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence. This first stand includes: a primer sequence a adjacent to, and 5' of, single-stranded primer sequence b; and a clamp sequence c adjacent to, and 5' of, primer sequence a, wherein clamp sequence c is not complementary to a first strand template sequence d', which is adjacent to, and 3' of, first strand template sequence a'. In some embodiments, the $T_{in}$ of combined sequence c-a (the hyphen is used in this context to denote the combined nucleic acid sequence made up of sequences c and a) in double-stranded form (i.e., c-a/c'-a'), is greater than that of combined sequence a-b, in double stranded form (i.e., a-b/a'-b'). This is readily achieved, e.g., by making combined sequence c-a longer and/or more GC-rich than combined sequence a-b, and/or designing combined sequence c-a to include more stabilizing bases than combined sequence a-b (the requirement for "more" includes the situation in which sequence a-b contains no G-C basepairs and/or no stabilizing bases). Alternatively or in addition, combined sequence a-b can be designed to include more destabilizing bases than combined sequence c-a (the requirement for "more" includes the situation in which sequence c-a contains no destabilizing bases). In some embodiments, a'-c' is blocked to extension at its 3' end.

The forward two-primer set can be employed with a simple conventional reverse primer for a hemi-nested amplification or with a reverse two-primer set.

Referring to FIG. 3, the inner primer in a reverse two-primer set includes a single-stranded primer sequence f that specifically hybridizes to first template strand sequence f, wherein I' is adjacent to, and 5' of, e', and wherein single-stranded primer sequence f is linked at its 5' end to a first strand of a double-stranded primer sequence. This first stand includes: a primer sequence e adjacent to, and 5' of, single-stranded primer sequence f; and a clamp sequence g adjacent to, and 5' of, primer sequence e, wherein clamp sequence g is not complementary to a first strand template sequence h', which is adjacent to, and 3' of, first strand template sequence e'. In some embodiments, the $T_m$ of combined sequence g-e, in double-stranded form (i.e., g-e/g'-e') is greater than that of combined sequence e-f, in double-stranded form (i.e., e-f/e'-f) This is readily achieved, e.g., by making combined sequence g-e longer and/or more GC-rich than combined sequence e-f, and/or designing combined sequence the $T_m$ of combined sequence g-e, in double-stranded form is greater than that of combined sequence e-f, in double-stranded form to include more stabilizing bases than combined sequence e-f (the requirement for "more" includes the situation in which sequence e-f contains no G-C base pairs and/or no stabilizing bases). Alternatively or in addition, combined sequence e-f can be designed to include more destabilizing bases than combined sequence g-e (the requirement for "more" includes the situation in which sequence g-e contains no destabilizing bases). In some embodiments, e'-g' is blocked to extension at its 3' end.

In some embodiments, clamp sequence(s) c and g, if present, is/are not capable of being copied during amplification. RNA or an RNA analog, e.g., a hydrolysis-resistant RNA analog, can be employed to provide the required base pairing to form the double-stranded clamp sequence without being copied by a DNA-dependent polymerase during amplification. The most common RNA analogues is 2'-O-methyl-substituted RNA. Other nucleic acid analogues that can base pair specifically but cannot be copied include locked nucleic acid (LNA) or BNA (Bridged Nucleic Acid), morpholino, and peptide nucleic acid (PNA). Although these oligonucleotides have a different backbone sugar or, in the case of PNA, an amino acid residue in place of the ribose phosphate, they still bind to RNA or DNA according to Watson and Crick pairing, but are immune to nuclease activity. They cannot be synthesized enzymatically and can only be obtained synthetically using phosphoramidite strategy or, for PNA, methods of peptide synthesis.

If desired, the clamp sequence c can be covalently linked to complementary sequence c' so that a-c/a-c' is formed from a hairpin structure; however, this is not necessary for efficient formation of the double-stranded clamp portion of the primer. Similarly, the clamp sequence g can, but need not, be covalently linked to complementary sequence g' so that e-g/e'-g' is formed from a hairpin structure.

Primers of a Three-Primer Set

In some embodiments, a third primer may be employed at one or both ends of a target nucleic acid sequence to further increase the number of copies produced in each cycle of amplification. FIGS. 4 and 5 show illustrative "forward" and "reverse" three-primer sets. A three-primer set includes an outer primer as discussed above and an intermediate primer that is essentially the same in structure as the inner primer discussed above. The additional primer is an inner primer which is designed to hybridize to the template strand 5' of the intermediate primer.

The inner primer in a forward three-primer set includes a single-stranded primer sequence b that specifically hybridizes to first template strand sequence b', wherein b' is adjacent to, and 5' of, a'. Single-stranded primer sequence b is linked at its 5' end to a first strand of a double-stranded primer sequence comprising: a primer sequence a adjacent to, and 5' of, single-stranded primer sequence b, a primer sequence d adjacent to, and 5' of, primer sequence a, and a clamp sequence c2 adjacent to, and 5' of, primer sequence d, wherein clamp sequence c2 is not complementary to first strand template sequence i'. Clamp sequence c2 can be the same as, or different from, the clamp sequence used in the inner primer (c1). In preferred embodiments, c1 and c2 are different sequences. Similar considerations apply to the design of the inner primer in a three-primer set as discussed above with respect to the inner primer in a two primer set, and the inner primer in a reverse three-primer set (shown in FIG. 5) has the same structure as the inner primer in a forward three-primer set. One or more (or all) of the clamp oligonucleotides (d'-c1' and a'-d'-c2' in FIG. 4 and h'-g1' and e'-h'-g2' in FIG. 5) can be blocked to extension at their 3' ends. The forward three-primer set can be employed with a simple conventional reverse primer for a hemi-nested amplification, with a reverse two-primer set, or with a reverse three-primer set.

In some embodiments, the order of primer annealing and extension is controlled based on the $T_m$ of the primer sequences so that any primer that is "inner" with respect to another primer anneals and begins extension before that other primer. Thus, for example, in a two-primer set, the inner primer anneals and begins extension before the outer primer, and in a three-primer set, the inner primer anneals and begins extension before the intermediate primer, and the intermediate primer anneals and begins extension before the outer primer. For example, in the embodiment shown in FIG. 4, the $T_m$'s of the primer sequences would have the relationship: $T_m$ of d<$T_m$ of a<$T_m$ of b. In the embodiment shown in FIG. 5, the $T_m$'s of the primer sequences would have the relationship: $T_m$ of h<$T_m$ of e<$T_m$ of f. As noted above, $T_m$'s are a function of sequence length, C-G content, and the, optional, presence of stabilizing and/or destabilizing bases.

Further nested primers can be designed based on the principles discussed above.

Polymerase

The disclosed methods make the use of a polymerase for amplification. In some embodiments, the polymerase is a DNA polymerase that lacks a 5' to 3' exonuclease activity. The polymerase is used under conditions such that the strand extending from a first primer can be displaced by polymerization of the forming strand extending from a second primer that is "outer" with respect to the first primer. Conveniently, the polymerase is capable of displacing the strand complementary to the template strand, a property termed "strand displacement." Strand displacement results in synthesis of multiple copies of the target sequence per template molecule. In some embodiments, the DNA polymerase for use in the disclosed methods is highly processive. Exemplary DNA polymerases include variants of Taq DNA polymerase that lack 5' to 3' exonuclease activity, e.g., the Stoffel fragment of Taq DNA polymerase (ABI), SD polymerase (Bioron), mutant Taq lacking 5' to 3' exonuclease activity described in U.S. Pat. No. 5,474,920, Bca polymerase (Takara), Pfx50 polymerase (Invitrogen), Tfu DNA polymerase (Qbiogene). If thermocycling is to be carried out (as in PCR), the DNA polymerase is preferably a thermostable DNA polymerase. Table 2 below lists polymerases available from New England Biolabs that have no 5' to 3' exonuclease activity, but that have strand displacement activity accompanied by thermal stability.

TABLE 2

Thermostable Stand-Displacing Polymerases Lacking 5' to 3' Exonuclease Activity

| Polymerase | 5'->3' Exonuclease | Strand Displacement | Thermal Stability |
|---|---|---|---|
| Bst DNA Polymerase, Large Fragment | − | ++++ | + |
| Bsu DNA Polymerase, Large Fragment | − | ++ | − |
| DEEP VENT$_R$ ™ DNA Polymerase | − | ++ | ++++ |
| DEEP VENT$_R$ ™ (exo−) DNA Polymerase | − | +++ | ++++ |
| Klenow Fragment (3'→5' exo−) | − | +++ | − |
| DNA Polymerase I, Large (Klenow) Fragment | − | ++ | − |
| M-MuLV Reverse Transcriptase | − | +++ | − |
| phi29 DNA Polymerase | − | +++++ | − |
| THERMINATOR ™ DNA Polymerase | − | + | ++++ |
| VENT$_R$ ® DNA Polymerase | − | ++$^e$ | +++ |
| VENT$_R$ ® (exo−) DNA Polymerase | − | +++$^e$ | +++ |

In some embodiments, the DNA polymerase comprises a fusion between Taq polymerase and a portion of a topoisomerase, e.g., TOPOTAQ™ (Fidelity Systems, Inc.).

Strand displacement can also be facilitated through the use of a strand displacement factor, such as a helicase. Any DNA polymerase that can perform strand displacement in the presence of a strand displacement factor is suitable for use in the disclosed method, even if the DNA polymerase does not perform strand displacement in the absence of such a factor. Strand displacement factors useful in the methods described herein include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)), single-stranded DNA binding proteins (SSB; Rigler and Romano, J. Biol. Chem. 270:8910-8919 (1995)), and calf thymus helicase (Siegel et al., J. Biol. Chem. 267:13629-13635 (1992)). Helicase and SSB are available in thermostable forms and therefore suitable for use in PCR.

Amplification

The primer sets described above are contacted with sample nucleic acids under conditions wherein the primers anneal to their template strands, if present. The desired nucleic acid amplification method is carried out using a DNA polymerase lacking 5'-3' exonuclease activity that is capable of strand displacement under the reaction conditions employed. This amplification produces amplicons that include the sequences of all primers employed in the amplification reaction. The primer sets can conveniently be added to the amplification mixture in the form of separate oligonucleotides. For example, the two-primer set can consist of three oligonucleotides (assuming that the inner primer does not include a hairpin structure) and the three-primer set can consist of five oligonucleotides (assuming that neither the inner, nor the intermediate, primers include a hairpin structure).

For hemi-nested amplification using a two-primer set, as described above, a rate of up to $3^{number\ of\ cycles}$ during the exponential phase of PCR can be achieved. Amplification using a hemi-nested two-primer set can reduce the number of amplification cycles required to detect a single-copy nucleic acid by about 12% to about 42% (e.g., by 37%). This facilitates detection of a single copy nucleic acid in a biological sample within about 23-27 amplification cycles (which might otherwise require 40 or more cycles). In some embodiments, hemi-nested, two-primer set PCR facilitates detection of a single copy nucleic acid in a biological sample in 23, 24, 25, 26, or 27 amplification cycles.

Table 3 below shows the number of cycles needed to amplify a single-copy nucleic acid to $10^{12}$ copies using the different embodiment described herein. For fully-nested amplification using a two-primer set, as described above, a rate of up to $6^{number\ of\ cycles}$ during the exponential phase of PCR can be achieved. Amplification using a fully-nested two-primer set can reduce the number of amplification cycles required to detect a single-copy nucleic acid by about 36% to about 66% (e.g., by 61%). This facilitates detection of a single copy nucleic acid in a biological sample within about 13-17 amplification cycles. In some embodiments, fully-nested, two-primer set PCR facilitates detection of a single copy nucleic acid in a biological sample in 13, 14, 15, 16, or 17 amplification cycles.

TABLE 3

Reduction in Number of Cycles Needed for Amplification as a Function of PCR Base

| PCR base | number of cycles needed to reach 10^12 copies | % reduction of cycles needed | upper bound reduction (+5%) | lower bound reduction (−25%) |
|---|---|---|---|---|
| 2 | 39.86 | na | na | na |
| 3 | 25.15 | 37% | 42% | 12% |
| 4 | 19.93 | 50% | 55% | 25% |
| 6 | 15.42 | 61% | 66% | 36% |
| 8 | 13.29 | 67% | 72% | 42% |

For hemi-nested amplification using a three-primer set, as described above, a rate of up to $4^{number\ of\ cycles}$ during the exponential phase of PCR can be achieved. Amplification using a hemi-nested three-primer set can reduce the number of amplification cycles required to detect a single-copy nucleic acid by about 25% to about 55% (e.g., by 50%). This facilitates detection of a single copy nucleic acid in a biological sample within about 20 amplification cycles (which might otherwise require 40 or more cycles). In some embodiments, hemi-nested, three-primer set PCR facilitates detection of a single copy nucleic acid in a biological sample in 18, 19, 20, 21, or 22 amplification cycles.

For fully-nested amplification using a three-primer set, as described above, a rate of up to $8^{number\ of\ cycles}$ during the exponential phase of PCR can be achieved. Amplification using a fully-nested three-primer set can reduce the number of amplification cycles required to detect a single-copy nucleic acid by about 42% to about 72% (e.g., by 67%). This facilitates detection of a single copy nucleic acid in a biological sample within about 11-15 amplification cycles. In some embodiments, fully-nested, three-primer set PCR facilitates detection of a single copy nucleic acid in a biological sample in 9, 10, 11, 12, or 13 amplification cycles.

In some embodiments, the amplification step is performed using PCR. For running real-time PCR reactions, reaction mixtures generally contain an appropriate buffer, a source of magnesium ions ($Mg^{2+}$) in the range of about 1 to about 10 mM, e.g., in the range of about 2 to about 8 mM, nucleotides, and optionally, detergents, and stabilizers. An example of one suitable buffer is TRIS buffer at a concentration of about 5 mM to about 85 mM, with a concentration of 10 mM to 30 mM preferred. In one embodiment, the TRIS buffer concentration is 20 mM in the reaction mix double-strength (2×) form. The reaction mix can have a pH range of from about 7.5 to about 9.0, with a pH range of about 8.0 to about 8.5 as typical. Concentration of nucleotides can be in the range of about 25 mM to about 1000 mM, typically in the range of about 100 mM to about 800 mM. Examples of dNTP concentrations are 100, 200, 300, 400, 500, 600, 700, and 800 mM. Detergents such as Tween 20, Triton X 100, and Nonidet P40 may also be included in the reaction mixture. Stabilizing agents such as dithiothreitol (DTT, Cleland's reagent) or mercaptoethanol may also be included. In addition, master mixes may optionally contain dUTP as well as uracil DNA glycosylase (uracil-N-glycosylase, UNG). A master mix is commercially available from Applied Biosystems, Foster City, Calif., (TaqMan® Universal Master Mix, cat. nos. 4304437, 4318157, and 4326708).

Labeling Strategies

Any suitable labeling strategy can be employed in the methods described herein. Where the reaction is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Pico Green (Molecular Probes, Inc., Eugene, Oreg.), Eva Green (Biotinum), ethidium bromide, and the like (see Zhu et al., 1994, *Anal. Chem.* 66:1941-48).

In some embodiments, one or more target-specific qPCR probes (i.e., specific for a target nucleotide sequence to be detected) is employed in the amplification mixtures to detect amplification products. By judicious choice of labels, analyses can be conducted in which the different labels are excited and/or detected at different wavelengths in a single reaction ("multiplex detection"). See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

In some embodiments, it may be convenient to include labels on one or more of the primers employed in in amplification mixture.

Exemplary Automation and Systems

In some embodiments, a target nucleic acid is detected using an automated sample handling and/or analysis platform. In some embodiments, commercially available automated analysis platforms are utilized. For example, in some embodiments, the GeneXpert® system (Cepheid, Sunnyvale, Calif.) is utilized.

The methods described herein are illustrated for use with the GeneXpert system. Exemplary sample preparation and analysis methods are described below. However, the present invention is not limited to a particular detection method or analysis platform. One of skill in the art recognizes that any number of platforms and methods may be utilized.

The GeneXpert® utilizes a self-contained, single use cartridge. Sample extraction, amplification, and detection may all be carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety for this description.)

Components of the cartridge include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection. A reaction tube enables very rapid thermal cycling.

In some embodiments, the GenXpert® system includes a plurality of modules for scalability. Each module includes a plurality of cartridges, along with sample handling and analysis components.

After the sample is added to the cartridge, the sample is contacted with lysis buffer and released nucleic acid is bound to a nucleic acid-binding substrate such as a silica or glass substrate. The sample supernatant is then removed and the nucleic acid eluted in an elution buffer such as a Tris/EDTA buffer. The eluate may then be processed in the cartridge to detect target genes as described herein. In some embodiments, the eluate is used to reconstitute at least some of the reagents, which are present in the cartridge as lyophilized particles.

In some embodiments, PCR is used to amplify and detect the presence of one or more target nucleic acids. In some embodiments, the PCR uses Taq polymerase with hot start function, such as AptaTaq (Roche).

In some embodiments, an off-line centrifugation is used to improve assay results with samples with low cellular content. The sample, with or without the buffer added, is centrifuged and the supernatant removed. The pellet is then resuspended in a smaller volume of supernatant, buffer, or other liquid. The resuspended pellet is then added to a GeneXpert® cartridge as previously described.

Kits

Also contemplated is a kit for carrying out the methods described herein. Such kits include one or more reagents useful for practicing any of these methods. A kit generally includes a package with one or more containers holding the reagents, as one or more separate compositions or, optionally, as an admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits preferably include instructions for carrying out one or more of the screening methods described herein. Instructions included in kits can be affixed to packaging material or can be included as a package insert. While the instructions are typically written or printed materials they are not limited to such. Any medium capable of storing such instructions and communicating them to an end user can be employed. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

Example 1: Confirmation of Effect of "Clamp" Oligo on Primer/Target Structure

An experiment was performed in which the Tm was measured of a primer oligo (although called a "primer," it was not used as such in this experiment) and a complimentary target sequence with and without the "clamp" oligo present. The target oligo was synthesized with a 5' fluorescent tag (fluorescein), and the primer incorporated a fluorescence quenching moiety (see FIG. 6). The c sequence includes a 2' O-methyl backbone. The oligo sequences tested are listed in Table 4 below. The Tm of the right hand-most double-helical region shown in the structures of FIG. 6 was measured by following the increase in fluorescence that results as temperature is increased and as the fluor and quencher are separated by melting of this double-helical region.

If the region of primer to target binding were, as indicated in FIG. 6A, limited by the clamp to a b/b' binding, then the Tm of that region would be predicted to be much lower than in the situation in FIG. 6B with ab/a'b' binding. In Table 4 below are listed the oligos used in this and the following experiment. In Table 5 are the predicted and observed Tm's for primer and target oligos, in the presence or absence of a clamp oligo.

TABLE 4

Oligonucleotides used

| Oligo no. | Sequence | Category |
|---|---|---|
| 16140 | 5'ggcgcuccggaccggcgTAGGCTGGTAACCAACCGCTGAAGGCA(U01)ACGG3' (note: lower case = 2'-O-methyl; U01 = dabcyl quencher-labeled uracil) (SEQ ID NO: 1) | primer |
| 16141 | ggcgcuccggaccggcgTAGGCTGGTAACCAACCGCTGAAGGCA(U01)A-3' (SEQ ID NO: 2) | primer |
| 16142 | 5'TGGTTACCAGCCTACGCCGGTCCGGAGCGCC3'block* (SEQ ID NO: 3) | clamp |
| 16145 | 5'Fluorescein-CCGTATGCCTTCAGCGGTTGGTTACCAGCCTACGCATT3' (SEQ ID NO: 4) | target |

TABLE 4-continued

Oligonucleotides used

| Oligo no. | Sequence | Category |
|---|---|---|
| 16146 | 5'Fluorescein-TATGCCTTCAGCGGTTGGTTACCAGCCTACGCATT3'<br>(SEQ ID NO: 5) | target |
| 16147 | 5'CGTAGGCTGGTAACC3'<br>(SEQ ID NO: 6) | flanking primer |
| 16148 | 5'GCGTAGGCTGGTAACC3'<br>(SEQ ID NO: 7) | flanking primer |
| 16149 | 5'GCGT(A01)GGCTGGT(A01)ACC3' (A01 = 2-aminopurine)<br>(SEQ ID NO: 8) | flanking primer |

*block = moiety that blocks extension

TABLE 5

$T_m$ measurements

| Primer | Target | Clamp | Predicted Tm (deg. C.) | Observed Tm (deg. C.) |
|---|---|---|---|---|
| 16140 | 16145 | None | 76.4 (ab/a'b') | 78.5 |
| 16141 | 16146 | None | 74.6 (ab/a'b') | 78.0 |
| 16140 | 16145 | 16142 | 68.3 (b/b') | 67.0 |
| 16141 | 16146 | 16142 | 62.0 (b/b') | 66.5 |

The conditions for all hybrid melt analysis were: 0.01 M tris-HCl, 0.05 M KCl and 0.006 M MgCl$_2$. All oligonucleotides were at 1 micromolar. The oligo mixtures in Table 4 above were heated to 95 deg. C. and cooled slowly to 45 deg. C. and fluorescein fluorescence monitored using the Cepheid SmartCycler™. The Tm was determined as temperature at which the rate of fluorescence change was maximal.

The Tm's of b/b' and ab/a'b' were predicted using software (www.idtdna.com/analyzer/Applications/OligoAnalyzer). The observed Tm's are consistent with a structure in which the region d'-a' in the target, in the presence of a clamp oligo, remains single-stranded and available for hybridization.

The presence of a flanking primer (16147 to 16149) also at 1 micromolar, as diagrammed in FIG. 7A, made little difference in measured measured Tm's.

Example II: Extensibility of Outer (Flanking) Primer

The extensibility of the outer (flanking) primer shown schematically in FIG. 7A was tested under the conditions shown in Table 6 in a PCR reaction.

TABLE 6

| Reaction | Flanking primer |
|---|---|
| 1 | 16147 |
| 2 | 16148 |
| 3 | 16149 |
| 4 | none |

All reactions contained 10 mM Tris-HCl, 0.125 mM each dATP, dTTP, dCTP and dGTP, 0.15 micromolar of primer oligo 16140 from table 1, above, 0.125 micromolar of target oligo 16145 from table 1, 0.125 micromolar of clamp oligo 16142 from table 1, 45 mM KCl, 3.5 mM MgCl$_2$, 14 units of AmpliTaqCS, which has DNA polymerase activity but neither 5' to 3' nor 3' to '5 exonuclease activity, and 15 units of antibody to Taq polymerase, which provides a temperature activated "hot-start" to the incorporation reaction.

0.125 mM or no flanking primer was added as per Table 6 above; reactions were monitored over time using the SmartCycler while raising the temperature to 95 degrees to separate the oligos and simultaneously activate the polymerase, then lowering the temperature to 60 degrees to allow the oligos to anneal and to allow any primer extension to occur. The results are shown in 6B. The three rising traces are separate reactions with slightly different clamps; the flat trace is without the outer (flanking), displacing primer present. These results indicate that a strand displacing reaction that displaces the quencher occurs when the outer (flanking) primer is present.

What is claimed is:

1. A nucleic acid primer set for amplifying a target nucleic acid in a sample, wherein the target nucleic acid comprises a first template strand and, optionally, a second template strand, wherein the second template strand is complementary to the first template strand, the primer set comprising oligonucleotides in the form of, or capable of forming, at least two first primers capable of hybridizing to the first template strand, wherein the at least two first primers comprise a first outer primer and a first inner primer, the first outer primer comprising a primer sequence a that specifically hybridizes to first template strand sequence a'; and the first inner primer comprising a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence comprising:

a primer sequence a adjacent to, and 5' of, single-stranded primer sequence b; and a clamp sequence c adjacent to, and 5' of, primer sequence a, wherein clamp sequence c is not complementary to a first strand template sequence d', which is adjacent to, and 3' of, first strand template sequence a', wherein combined sequence a-b contains more destabilizing bases than combined sequence c-a.

2. The primer set of claim 1, wherein the primer set additionally comprises at least one second primer capable of specifically hybridizing to the second template strand.

3. A method for amplifying a target nucleic acid in a sample, wherein the target nucleic acid comprises a first template strand and, optionally, a second template strand, wherein the second template strand is complementary to the first template strand, the method comprising:

(a) contacting the sample with:
   (i) at least two first primers capable of hybridizing to the first template strand, wherein the at least two first primers comprise a first outer primer and a first inner primer,
   the first outer primer comprising a primer sequence a that specifically hybridizes to first template strand sequence a'; and
   the first inner primer comprising a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence comprising:
      a primer sequence a adjacent to, and 5' of, single-stranded primer sequence b; and
      a clamp sequence c adjacent to, and 5' of, primer sequence a, wherein clamp sequence c is not complementary to a first strand template sequence d', which is adjacent to, and 3' of, first strand template sequence a', wherein combined sequence a-b contains more destabilizing bases than combined sequence c-a; and
   (ii) at least one second primer capable of specifically hybridizing to the second template strand,
   wherein the contacting is carried out under conditions wherein the primers anneal to their template strands, if present; and (b) amplifying the target nucleic acid, if present, using a DNA polymerase lacking 5'-3' exonuclease activity, under conditions where strand displacement occurs, to produce amplicons that comprise sequence extending from template sequence a' to the binding site for the second primer.

4. The primer set of claim 1, wherein the DNA polymerase comprises strand displacement activity.

5. The primer set of claim 1, wherein the $T_m$ of combined sequence c-a, in double-stranded form, is greater than that of combined sequence a-b, in double stranded form.

6. The primer set of claim 1, wherein combined sequence c-a is more GC-rich than combined sequence a-b, and/or contains more stabilizing bases.

7. The primer set of claim 1, wherein the second primer comprises oligonucleotides in the form of, or capable of forming, at least two second primers capable of hybridizing to the second template strand, wherein the at least two second primers comprise a second outer primer and a second inner primer, the second outer primer comprising a primer sequence e that specifically hybridizes to second template strand sequence e'; and the second inner primer comprising a single-stranded primer sequence f that specifically hybridizes to second template strand sequence f', wherein f' is adjacent to, and 5' of, e', and wherein single-stranded primer sequence f is linked at its 5' end to a first strand of a double-stranded primer sequence comprising:

a primer sequence e adjacent to, and 5' of, single-stranded primer sequence f; and a clamp sequence g adjacent to, and 5- of, primer sequence e, wherein clamp sequence g is not complementary to second strand template sequence h', which is adjacent to, and 3', of second strand template sequence e', wherein combined sequence e-f contains more destabilizing bases than combined sequence g-e.

8. The primer set of claim 7, wherein the $T_m$ of combined sequence g-e, in double-stranded form is greater than that of combined sequence e-f, in double-stranded form.

9. The primer set of claim 7, wherein combined sequence g-e is more GC-rich than combined sequence e-f, and/or contains more stabilizing bases.

10. A nucleic acid primer set for amplifying a target nucleic acid in a sample, wherein the target nucleic acid comprises a first template strand and, optionally, a second template strand, wherein the second template strand is complementary to the first template strand, the primer set comprising oligonucleotides in the form of, or capable of forming, at least three first primers capable of hybridizing to the first template strand, wherein the at least three first primers comprise a first outer primer, a first intermediate primer, and a first inner primer, the first outer primer comprising a primer sequence d that specifically hybridizes to first template strand sequence d';

the first intermediate primer comprising a primer sequence a that specifically hybridizes to first template strand sequence a', wherein a' is adjacent to, and 5' of, d', and wherein single-stranded primer sequence a is linked at its 5' end to a first strand of a double-stranded primer sequence comprising:

a primer sequence d adjacent to, and 5' of, single-stranded primer sequence a; and a clamp sequence c1 adjacent to, and 5- of, primer sequence d, wherein clamp sequence c1 is not complementary to a first strand template sequence i', which is adjacent to, and 3' of, first strand template sequence d'; and the first inner primer comprising a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence comprising:

a primer sequence a adjacent to, and 5' of, single-stranded primer sequence b;

a primer sequence d adjacent to, and 5' of, primer sequence a; and a clamp sequence c2 adjacent to, and 5' of, primer sequence d, wherein clamp sequence c2 is not complementary to first strand template sequence i', wherein c1 has a different sequence than c2.

11. A method for amplifying a target nucleic acid in a sample, wherein the target nucleic acid comprises a first template strand and, optionally, a second template strand, wherein the second template strand is complementary to the first template strand, the method comprising:

(a) contacting the sample with:

(i) at least three first primers capable of hybridizing to the first template strand, wherein the at least three first primers comprise a first outer primer, a first intermediate primer, and a first inner primer, the first outer primer comprising a primer sequence d that specifically hybridizes to first template strand sequence d';

the first intermediate primer comprising a primer sequence a that specifically hybridizes to first template strand sequence a', wherein a' is adjacent to, and 5' of, d', and wherein single-stranded primer sequence a is linked at its 5' end to a first strand of a double-stranded primer sequence comprising:

a primer sequence d adjacent to, and 5' of, single-stranded primer sequence a; and a clamp sequence c1 adjacent to, and 5- of, primer sequence d, wherein clamp sequence c1 is not complementary to a first strand template sequence i', which is adjacent to, and 3' of, first strand template sequence d'; and the first inner primer comprising a single-stranded primer sequence b that specifically hybridizes to first template strand sequence b', wherein b' is adjacent to, and 5' of, a', and wherein single-stranded primer sequence b is linked at its 5' end to a first strand of a double-stranded primer sequence comprising:

a primer sequence a adjacent to, and 5' of, single-stranded primer sequence b;

a primer sequence d adjacent to, and 5' of, primer sequence a; and a clamp sequence c2 adjacent to, and 5' of, primer sequence d, wherein clamp sequence c2 is not complementary to first strand template sequence i', wherein c1 has a different sequence than c2; and (ii) at least one second primer capable of specifically hybridizing to the second template strand, wherein the contacting is carried out under conditions wherein the primers anneal to their template strands, if present; and (b) amplifying the target nucleic acid, if present, using a DNA polymerase lacking 5'-3' exonuclease activity, under conditions where strand displacement occurs, to produce amplicons that comprise sequence extending from template sequence a' to the binding site for the second primer.

12. The method of claim 11, wherein the DNA polymerase comprises strand displacement activity.

13. The primer set of claim 10, wherein the $T_m$ of combined sequence c1-d, in double-stranded form, is greater than that of combined sequence d-a, in double-stranded form, and the $T_m$ of combined sequence c2-d-a, in double-stranded form, is greater than that of combined sequence d-a-b, in double-stranded form.

14. The primer set of claim 10, wherein combined sequence c1-$d$ is more GC-rich than combined sequence d-a, and/or contains more stabilizing bases, and combined sequence c2-$d$-$a$ is more GC-rich than combined sequence d-a-b, and/or contains more stabilizing bases than combined sequence d-a-b.

15. The method of claim 11, wherein said amplifying amplifies the target nucleic acid at the rate of up to $4^{number\ of\ cycles}$ during the exponential phase of PCR.

16. The method of claim 11, wherein said amplifying permits detection of a single copy nucleic acid in a biological sample within about 25%-55% fewer amplification cycles than would be required for said detection using only a single forward and a single reverse primer.

17. The primer set of claim 10, wherein the second primer comprises oligonucleotides in the form of, or capable of forming, at least three second primers capable of hybridizing to the second template strand, wherein the at least three second primers comprise a second outer primer, a second intermediate primer, and a second inner primer, the second outer primer comprising a primer sequence h that specifically hybridizes to second template strand sequence h';

the second intermediate primer comprising a single-stranded primer sequence e that specifically hybridizes to second template strand sequence e', wherein e' is adjacent to, and 5' of, h', and wherein single-stranded primer sequence e is linked at its 5' end to a first strand of a double-stranded primer sequence comprising:
  a primer sequence h adjacent to, and 5' of, single-stranded primer sequence e; and
  a clamp sequence g1 adjacent to, and 5' of, primer sequence h, wherein clamp sequence g1 is not complementary to a second strand template sequence j', which is adjacent to, and 3', of second strand template sequence h'; and the second inner primer comprising a single-stranded primer sequence f that specifically hybridizes to first template strand sequence f', wherein f' is adjacent to, and 5' of, e', and wherein single-stranded primer sequence f is linked at its 5' end to a first strand of a double-stranded primer sequence comprising:
  a primer sequence e adjacent to, and 5' of, single-stranded primer sequence f;
  a primer sequence h adjacent to, and 5' of, primer sequence e; and
  a clamp sequence g2 adjacent to, and 5' of, primer sequence h, wherein clamp sequence c2 is not complementary to first strand template sequence j'.

18. The primer set of claim 17, wherein the $T_m$ of combined sequence g1-$h$, in double-stranded form, is greater than that of combined sequence h-e, in double-stranded form, and the $T_m$ of combined sequence g2-$h$-$e$, in double-stranded form, is greater than that of combined sequence h-e-f, in double-stranded form.

19. The primer set of claim 17, wherein combined sequence g1-$h$ is more GC-rich than combined sequence h-e, and/or contains more stabilizing bases, and combined sequence g2-$h$-$e$ is more GC-rich than combined sequence h-e-f, and/or contains more stabilizing bases than combined sequence h-e-f.

20. The method of claim 12, wherein said amplifying amplifies the target nucleic acid at the rate of up to $8^{number\ of\ cycles}$ during the exponential phase of PCR.

21. The method of claim 12, wherein said amplifying permits detection of a single copy nucleic acid in a biological sample within about 42%-72% fewer amplification cycles than would be required for said detection using only a single forward and a single reverse primer.

22. The primer set of claim 17, wherein clamp sequences c1, c2, g1, and g2 are not capable of being copied during amplification.

23. The primer set of claim 22, wherein clamp sequences c1, c2, g1, and g2 each comprise 2'-O-methyl RNA.

24. The primer set of claim 17, wherein:
the double-stranded primer sequence of the first inner primer and the first intermediate primer; and/or
the second inner primer and the second intermediate primer, if present,
does/do not comprise a hairpin sequence.

25. The primer set of claim 17, wherein:
the double-stranded primer sequence of the first inner primer comprises a hairpin sequence in which clamp sequence c2 is linked to complementary sequence c2'; and/or
the double-stranded primer sequence of the first intermediate primer comprises a hairpin sequence in which clamp sequence c1 is linked to complementary sequence c1'; and/or
the double-stranded primer sequence of the second inner primer, if present, comprises a hairpin sequence in which clamp sequence g2 is linked to complementary sequence g2'; and/or
the double-stranded primer sequence of the second intermediate primer, if present, comprises a hairpin sequence in which clamp sequence g1 is linked to complementary sequence g1'.

26. The primer set of claim 10, wherein combined sequence d-a contains more destabilizing bases than combined sequence c1-$d$, and/or combined sequence d-a-b contains more destabilizing bases than combined sequence c2-$d$-$a$.

27. The primer set of claim 17, wherein combined sequence h-e contains more destabilizing bases than combined sequence g1-$h$, and/or combined sequence h-e-f contains more destabilizing bases than combined sequence g2-$h$-$e$.

* * * * *

SEQUENCE LISTING

<160> NUMBER OF SEQ ID NOS: 8

<210> SEQ ID NO 1
<211> LENGTH: 49
<212> TYPE: DNA
<213> ORGANISM: Artificial
<220> FEATURE:
<223> OTHER INFORMATION: Primer
<220> FEATURE:
<221> NAME/KEY: modified_base
<222> LOCATION: (1)..(17)
<223> OTHER INFORMATION: 2'-O-methyl
<220> FEATURE:
<221> NAME/KEY: modified_base
<222> LOCATION: (6)..(6)
<223> OTHER INFORMATION: uracil
<220> FEATURE:

```
<221> NAME/KEY: modified_base
<222> LOCATION: (45)..(45)
<223> OTHER INFORMATION: dabcyl quencher-labeled uracil

<400> SEQUENCE: 1
ggcgctccgg accggcgtag gctggtaacc aaccgctgaa ggcatacgg          49

<210> SEQ ID NO 2
<211> LENGTH: 46
<212> TYPE: DNA
<213> ORGANISM: Artificial
<220> FEATURE:
<223> OTHER INFORMATION: Primer
<220> FEATURE:
<221> NAME/KEY: modified_base
<222> LOCATION: (1)..(17)
<223> OTHER INFORMATION: 2'-O-methyl
<220> FEATURE:
<221> NAME/KEY: modified_base
<222> LOCATION: (6)..(6)
<223> OTHER INFORMATION: uracil
<220> FEATURE:
<221> NAME/KEY: modified_base
<222> LOCATION: (45)..(45)
<223> OTHER INFORMATION: dabcyl quencher-labeled uracil

<400> SEQUENCE: 2
ggcgctccgg accggcgtag gctggtaacc aaccgctgaa ggcata            46

<210> SEQ ID NO 3
<211> LENGTH: 31
<212> TYPE: DNA
<213> ORGANISM: Artificial
<220> FEATURE:
<223> OTHER INFORMATION: Clamp

<400> SEQUENCE: 3
tggttaccag cctacgccgg tccggagcgc c                             31

<210> SEQ ID NO 4
<211> LENGTH: 38
<212> TYPE: DNA
<213> ORGANISM: Artificial
<220> FEATURE:
<223> OTHER INFORMATION: Target

<400> SEQUENCE: 4
ccgtatgcct tcagcggttg gttaccagcc tacgcatt                      38

<210> SEQ ID NO 5
<211> LENGTH: 35
<212> TYPE: DNA
<213> ORGANISM: Artificial
<220> FEATURE:
<223> OTHER INFORMATION: Target

<400> SEQUENCE: 5
tatgccttca gcggttggtt accagcctac gcatt                         35

<210> SEQ ID NO 6
<211> LENGTH: 15
<212> TYPE: DNA
<213> ORGANISM: Artificial
<220> FEATURE:
<223> OTHER INFORMATION: Flanking primer

<400> SEQUENCE: 6
cgtaggctgg taacc                                               15
```

```
<210> SEQ ID NO 7
<211> LENGTH: 16
<212> TYPE: DNA
<213> ORGANISM: Artificial
<220> FEATURE:
<223> OTHER INFORMATION: Flanking primer

<400> SEQUENCE: 7
gcgtaggctg gtaacc                                               16

<210> SEQ ID NO 8
<211> LENGTH: 16
<212> TYPE: DNA
<213> ORGANISM: Artificial
<220> FEATURE:
<223> OTHER INFORMATION: Flanking primer
<220> FEATURE:
<221> NAME/KEY: modified_base
<222> LOCATION: (5)..(5)
<223> OTHER INFORMATION: 2-aminopurine
<220> FEATURE:
<221> NAME/KEY: modified_base
<222> LOCATION: (13)..(13)
<223> OTHER INFORMATION: 2-aminopurine

<400> SEQUENCE: 8
gcgtaggctg gtaacc                                               16
```